(12) United States Patent
O'Mara

(10) Patent No.: US 7,552,729 B2
(45) Date of Patent: Jun. 30, 2009

(54) INTUBATION DEVICE AND METHOD

(75) Inventor: Sean T. O'Mara, Winchester, VA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 577 days.

(21) Appl. No.: 10/086,940

(22) Filed: Mar. 1, 2002

(65) Prior Publication Data
US 2002/0195103 A1 Dec. 26, 2002

Related U.S. Application Data

(60) Provisional application No. 60/273,795, filed on Mar. 5, 2001.

(51) Int. Cl.
A61M 16/00 (2006.01)
A62B 9/04 (2006.01)

(52) U.S. Cl. .............. 128/200.26; 128/207.14; 128/202.27

(58) Field of Classification Search ............ 128/200.26, 128/205.23, 207.14, 207.15, 207.16, 207.29, 128/912, 202.29, DIG. 29; 600/114, 117, 600/129, 139; 604/19, 93.01, 102.03, 164.05
See application file for complete search history.

(56) References Cited

U.S. PATENT DOCUMENTS

| 2,463,149 | A | * | 3/1949 | Caine | 128/200.26 |
| 2,516,494 | A | * | 7/1950 | Wallace | 600/129 |
| 3,256,875 | A | * | 6/1966 | Tsepelev et al. | 600/148 |
| 3,297,022 | A | * | 1/1967 | Wallace | 600/172 |
| 3,677,262 | A | | 7/1972 | Zukowski | 128/6 |

(Continued)

FOREIGN PATENT DOCUMENTS

EP 0 131 659 A1 1/1985

(Continued)

OTHER PUBLICATIONS

Products—LMA Fastrachtm URL=http://www.1mana.com/prod/components/products/lma_fastrach.html, download date Mar. 1, 2002.

(Continued)

Primary Examiner—Justine R. Yu
Assistant Examiner—Annette F Dixon
(74) Attorney, Agent, or Firm—Elizabeth Arwine

(57) ABSTRACT

In one embodiment, an apparatus is characterized by an intubation-tube placement device; and an intubation tube secured to the intubation-tube placement device. In another embodiment, an apparatus is characterized by an intubation-tube placement device; and an anti-perforation device coupled to the intubation-tube placement device. In another embodiment, an apparatus is characterized by an intubation-tube placement device; and at least one tactile-accentuator flap coupled to the intubation-tube placement device. In another embodiment, an apparatus is characterized by an intubation-tube placement device; and a handle affixed to the intubation-tube placement device. In another embodiment, a method is characterized by inserting an intubation-tube placement device, secured to an intubation tube, into a patient's oral cavity; forcing the intubation-tube placement device through the patient's vocal cords; and axially sliding the intubation tube along the intubation-tube placement device such that the intubation tube follows the intubation-tube placement device through the patient's vocal cords.

43 Claims, 12 Drawing Sheets

U.S. PATENT DOCUMENTS

| | | | | |
|---|---|---|---|---|
| 3,799,150 A * | 3/1974 | Bonnet | .................. | 600/128 |
| 3,957,055 A * | 5/1976 | Linder et al. | .................. | 128/200.26 |
| 4,185,639 A * | 1/1980 | Linder | .................. | 128/200.26 |
| 4,279,245 A * | 7/1981 | Takagi et al. | .................. | 600/139 |
| 4,449,522 A * | 5/1984 | Baum | .................. | 128/200.26 |
| 4,469,091 A * | 9/1984 | Slanetz, Jr. | .................. | 600/117 |
| 4,471,776 A * | 9/1984 | Cox | .................. | 128/207.15 |
| 4,593,687 A * | 6/1986 | Gray | .................. | 128/200.26 |
| 4,846,153 A * | 7/1989 | Berci | .................. | 600/109 |
| 4,848,331 A * | 7/1989 | Northway-Meyer | .... | 128/200.26 |
| 4,938,746 A * | 7/1990 | Etheredge et al. | .................. | 604/265 |
| 4,949,716 A * | 8/1990 | Chenoweth | .................. | 128/207.14 |
| 5,052,386 A | 10/1991 | Fischer, Jr. | .................. | 128/207.15 |
| 5,058,577 A | 10/1991 | Six | .................. | 128/200.26 |
| 5,183,031 A * | 2/1993 | Rossoff | .................. | 600/131 |
| 5,197,465 A * | 3/1993 | Montgomery | .................. | 128/207.29 |
| 5,250,033 A * | 10/1993 | Evans et al. | .................. | 604/160 |
| 5,263,478 A * | 11/1993 | Davis | .................. | 128/207.14 |
| 5,279,610 A | 1/1994 | Park et al. | .................. | 606/108 |
| 5,287,848 A * | 2/1994 | Cubb et al. | .................. | 128/200.26 |
| 5,329,940 A * | 7/1994 | Adair | .................. | 128/200.26 |
| 5,339,808 A | 8/1994 | Don Michael | .................. | 128/207.15 |
| 5,400,771 A * | 3/1995 | Pirak et al. | .................. | 600/109 |
| 5,456,250 A * | 10/1995 | Hissong | .................. | 128/207.14 |
| 5,546,937 A * | 8/1996 | Stuart et al. | .................. | 128/207.15 |
| 5,595,172 A * | 1/1997 | Reese | .................. | 128/200.26 |
| 5,607,386 A * | 3/1997 | Flam | .................. | 600/120 |
| 5,636,625 A * | 6/1997 | Miyagi et al. | .................. | 128/200.26 |
| 5,676,635 A | 10/1997 | Levin | .................. | 600/120 |
| 5,715,816 A | 2/1998 | Mainiero et al. | .................. | 128/633 |
| 5,749,357 A | 5/1998 | Linder | .................. | 128/200.26 |
| 5,791,338 A | 8/1998 | Merchant et al. | .................. | 128/200.26 |
| 5,803,080 A | 9/1998 | Freitag | .................. | 128/207.14 |
| 5,803,898 A | 9/1998 | Bashour | .................. | 600/120 |
| 5,819,727 A | 10/1998 | Linder | .................. | 128/200.26 |
| 5,842,466 A * | 12/1998 | Selman | .................. | 128/200.26 |
| 5,846,183 A * | 12/1998 | Chilcoat | .................. | 600/136 |
| 5,873,362 A * | 2/1999 | Parker | .................. | 128/207.14 |
| 5,896,858 A | 4/1999 | Brain | .................. | 128/207.15 |
| 5,919,183 A | 7/1999 | Field | .................. | 604/530 |
| 6,062,223 A | 5/2000 | Palazzo et al. | .................. | 128/207.15 |
| 6,079,413 A * | 6/2000 | Baran | .................. | 128/207.14 |
| 6,146,402 A | 11/2000 | Munoz | .................. | 606/194 |
| 6,286,509 B1 | 9/2001 | Nash et al. | .................. | 128/207.14 |
| 6,743,234 B2 * | 6/2004 | Burkus et al. | .................. | 606/90 |
| 6,814,698 B2 * | 11/2004 | Barthel et al. | .................. | 600/139 |
| 6,820,614 B2 * | 11/2004 | Bonutti | .................. | 128/200.26 |

FOREIGN PATENT DOCUMENTS

| | | |
|---|---|---|
| EP | 0 594 335 A1 | 4/1994 |
| WO | WO 90/06077 | 6/1990 |

OTHER PUBLICATIONS

Laryngeal Mask Airway Web Page URL=http://doyle.ibme.utoronto.ca/lma/, download date Mar. 1, 2002.

\* cited by examiner

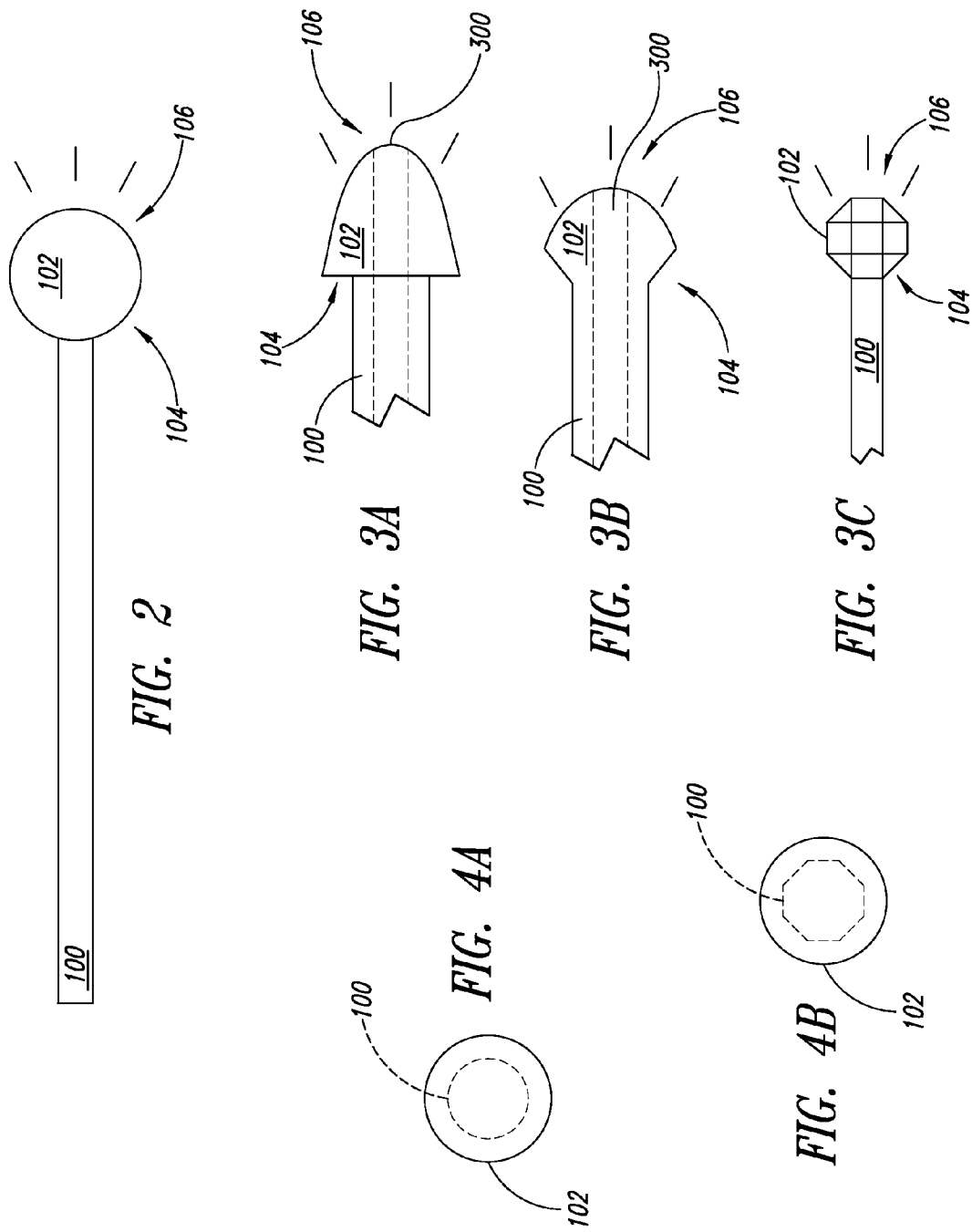

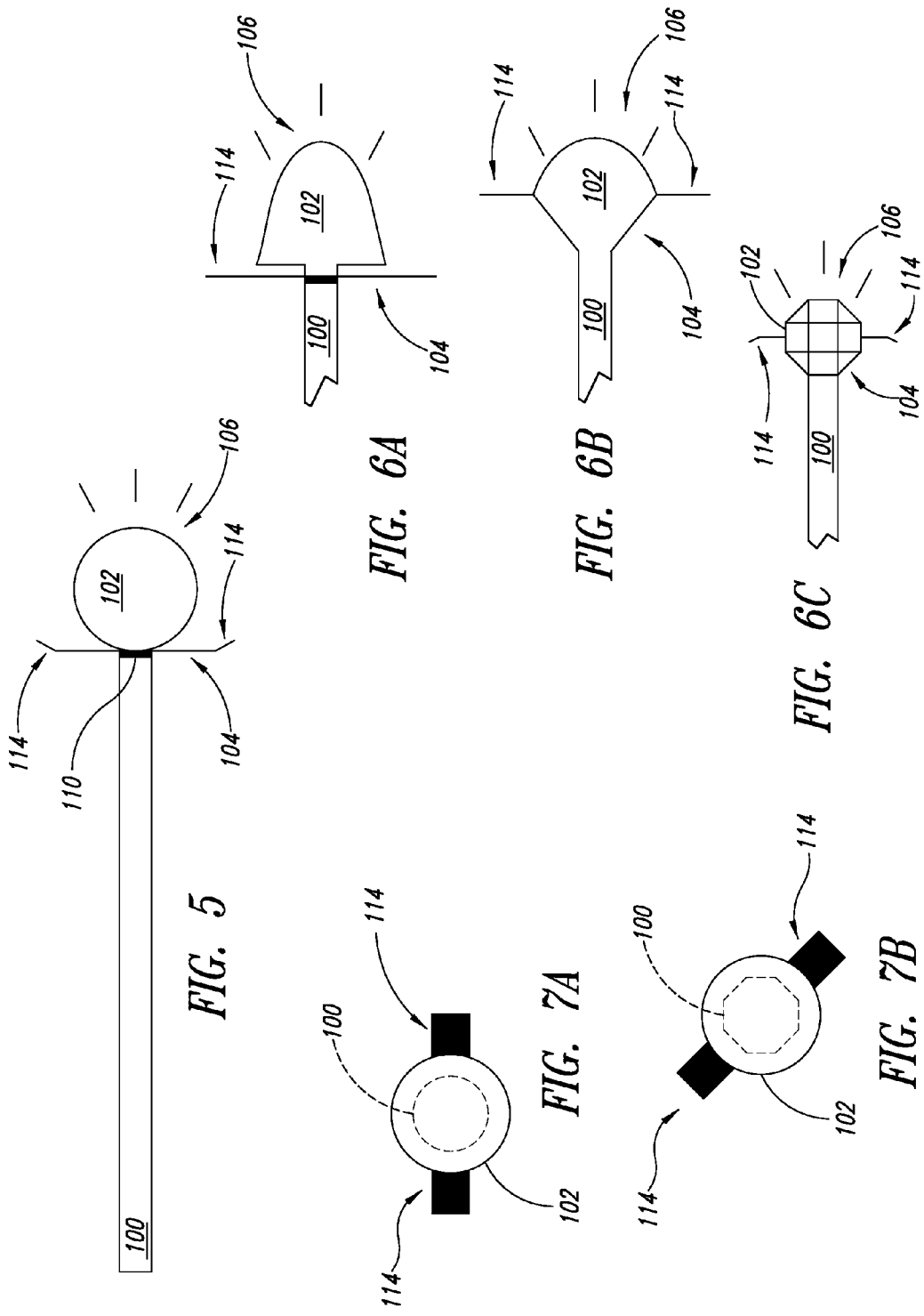

INTUBATION DEVICE AND METHOD

CROSS-REFERENCE TO RELATED APPLICATION

This application claims the benefit under 35 U.S.C. §119(e) of U.S. Provisional Patent Application No. 60/273,795 filed 5, Mar. 2001, said provisional patent application hereby incorporated by reference, in its entirety, into the detailed description portion of the present application. The incorporated-by-reference provisional patent application has been incorporated into the detailed description portion of the present application because the incorporated-by-reference provisional patent application described aspects of both the related art and the present patent application under a "background information" section; however, the description of aspects of the present patent application under the "background information" section of the provisional patent application is in no way an admission that such related art or aspects of the present invention constituted "prior art". In fact, several aspects of the present patent application predate the related-art aspects described in the provisional patent application. Accordingly, the foregoing statements constitute public notice that the provisional patent application was intended to contain no admissions related to prior art whatsoever.

STATEMENT REGARDING GOVERNMENT INTEREST

The government has certain rights in this invention.

BACKGROUND OF THE INVENTION

1. Field of the Invention

The present invention relates, in general, to intubation devices and methods.

2. Description of the Related Art

Intubation is the operation of inserting a tube into an animal's hollow organ or body passage to keep the organ or body passage open. One common example of intubation is endotracheal intubation, wherein a breathing tube is placed within the trachea of an animal. While endotracheal intubation will be described herein for sake of clarity, it is to be understood that the teachings herein are not limited to endotracheal intubation, but may instead be extended to other types of intubation.

The operation of endotracheal intubation may be described as follows. First, a patient's head is positioned, and mouth is opened, to allow a straight line of access from the mouth to the vocal cords (e.g., by placing a pillow under the head and neck of the patient). Second, the blade of a laryngoscope (a device which typically consists of a blade, a light source, and a handle) is introduced into the right-hand side of the patient's mouth, and the blade is used to sweep the tongue to the left. Third, the blade is advanced until the right tonsil is reached, at which point the health care provider sweeps the blade toward the midline of the patient's body—this brings the patient's epiglottis into view. Fourth, the health care provider advances the laryngoscope blade until it reaches the base of the epiglottis. Fifth, the health care provider levers the laryngoscope such that the epiglottis is moved toward the top of the patient's head such that the vocal cords of the patient come into view. Sixth, the health care provider advances the endotracheal tube through the vocal cords, until the inflatable cuff of the endotracheal tube has traversed the patient's vocal cords. Seventh, the health care provider inflates the inflatable cuff of the endotracheal tube which holds the endotracheal tube in the patient's trachea. Eighth, the health care provider secures the endotracheal tube somewhere inside the patient's mouth (typically, to the patient's upper jaw), and the operation of endotracheal intubation is considered completed.

BRIEF SUMMARY OF THE INVENTION

The inventor named herein has devised intubation devices and related methods.

In one embodiment, an apparatus is characterized by an intubation-tube placement device; and an intubation tube secured to the intubation-tube placement device.

In another embodiment, an apparatus is characterized by an intubation-tube placement device; and an anti-perforation device coupled to the intubation-tube placement device.

In another embodiment, an apparatus is characterized by an intubation-tube placement device; and at least one tactile-accentuator flap coupled to the intubation-tube placement device.

In another embodiment, an apparatus is characterized by an intubation-tube placement device; and a handle affixed to the intubation-tube placement device.

In another embodiment, a method is characterized by inserting an intubation-tube placement device, secured to an intubation tube, into a patient's oral cavity; forcing the intubation-tube placement device through the patient's vocal cords; and axially sliding the intubation tube along the intubation-tube placement device such that the intubation tube follows the intubation-tube placement device through the patient's vocal cords.

The foregoing is a summary and thus contains, by necessity, simplifications, generalizations and omissions of detail; consequently, those skilled in the art will appreciate that the summary is illustrative only and is NOT intended to be in any way limiting. Other aspects, inventive features, and advantages of the devices and/or processes described herein, as defined solely by the claims, will become apparent in the non-limiting detailed description set forth herein.

BRIEF DESCRIPTION OF THE SEVERAL VIEWS OF THE DRAWING(S)

FIG. 1A, shows a side-plan view of an intubation-tube placement device 100 secured to an intubation tube 116.

FIG. 1B shows that another implementation of an intubation-tube placement device 100 secured to an intubation tube 116 is characterized by an intubation-placement-device guide 120 integral with the intubation tube 116, where the intubation-placement-device guide 120 has a hole through which the intubation-tube placement device 100 has been inserted.

FIG. 2 depicts a side-plan isolation view of an anti-perforation device 102 coupled to an intubation-tube placement device 100.

FIG. 3A shows a side-plan isolation view of an alternate embodiment of an anti-perforation device 102 coupled to an intubation-tube placement device 100.

FIG. 3B depicts a side-plan isolation view of an alternate embodiment of an anti-perforation device 102 coupled to an intubation-tube placement device 100.

FIG. 3C illustrates a side-plan isolation view of an alternate embodiment of an anti-perforation device 102 coupled to an intubation-tube placement device 100.

FIG. 4A shows a front-plan view of an anti-perforation device 102 coupled to an intubation-tube placement device 100.

FIG. 4B depicts a front-plan view of an anti-perforation device 102 coupled to an intubation-tube placement device 100.

FIG. 5 shows a side-plan view of tactile-accentuator flaps 114 coupled to an intubation-tube placement device 100.

FIG. 6A depicts a side-plan isolation view of an alternate implementation of tactile-accentuator flaps 114 coupled to an intubation-tube placement device 100.

FIG. 6B illustrates a side-plan isolation view of an alternate implementation of tactile-accentuator flaps 114 coupled to an intubation-tube placement device 100.

FIG. 6C shows a side-plan isolation view of an alternate implementation of tactile-accentuator flaps 114 coupled to an intubation-tube placement device 100.

FIGS. 7A and 7B show structures substantially analogous to those depicted in FIGS. 4A and 4B, to which have been affixed tactile-accentuator flaps 114.

Figure 9:
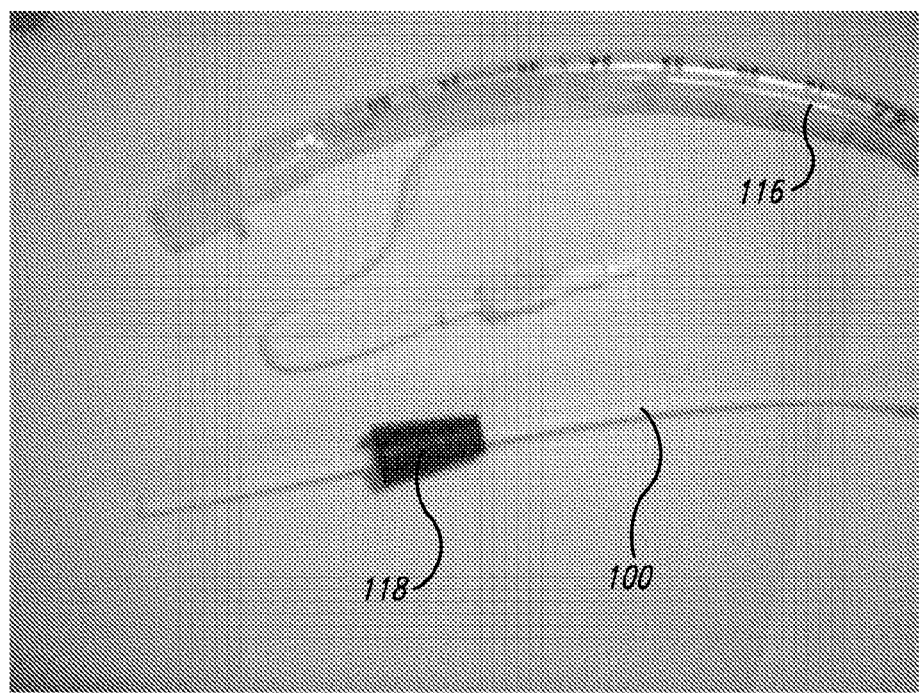

FIG. 9 shows a perspective view of an intubation tube 116, an intubation-tube placement device 100, and a rubber stopper 118 in disassembled form.

Figure 10:
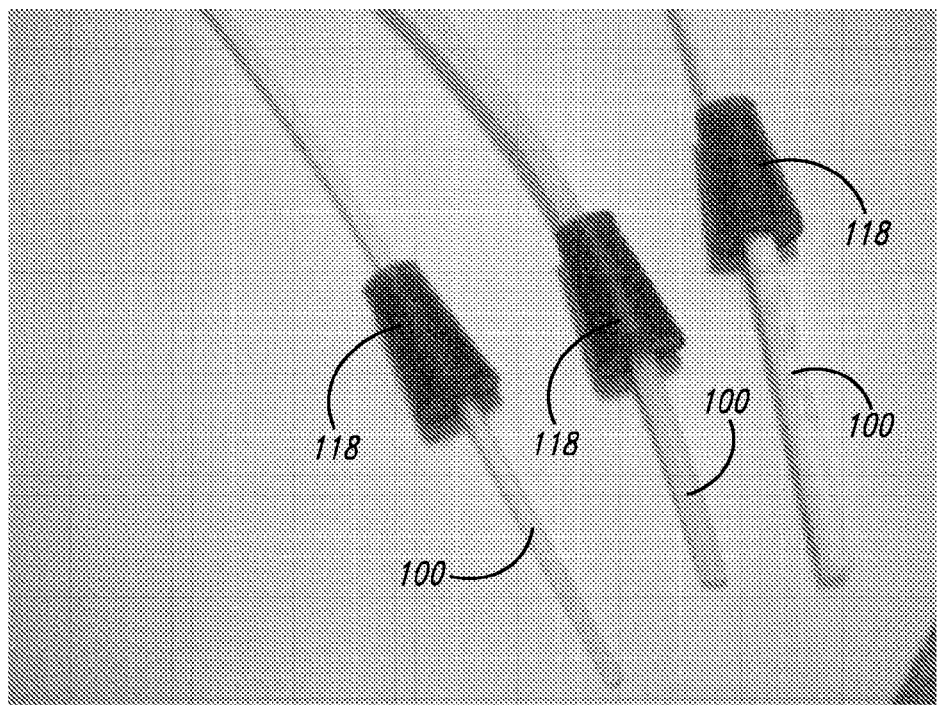

FIG. 10 depicts a top-plan view of three different-sized implementations of a rubber stopper 118, and an intubation-tube placement device 100.

Figure 11:
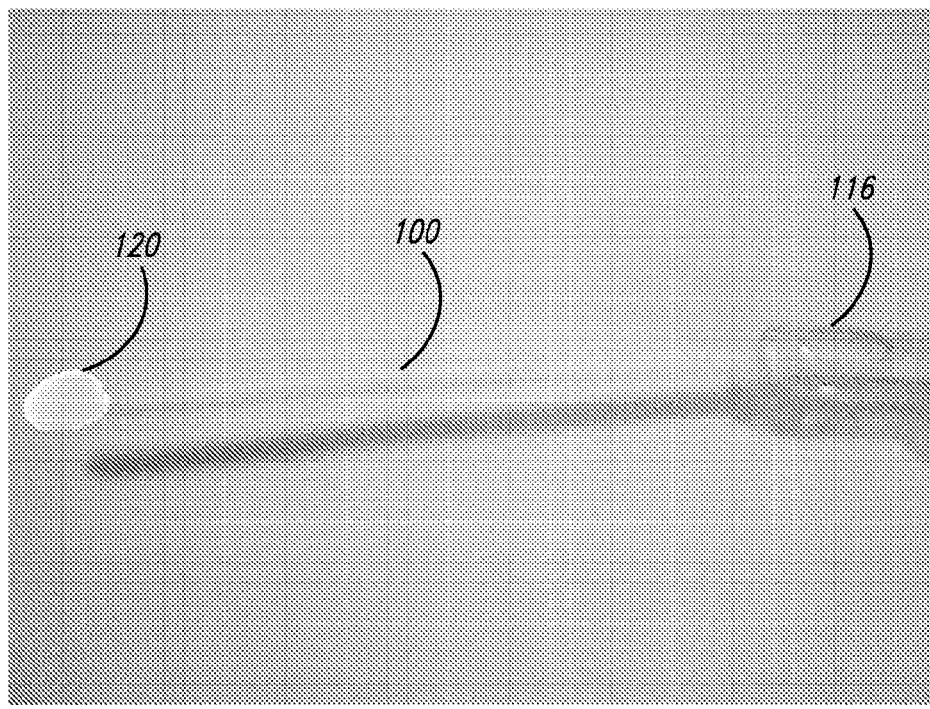

FIG. 11 illustrates a side-plan view of an intubation-tube placement device 100 internal to intubation tube 116.

Figure 13:
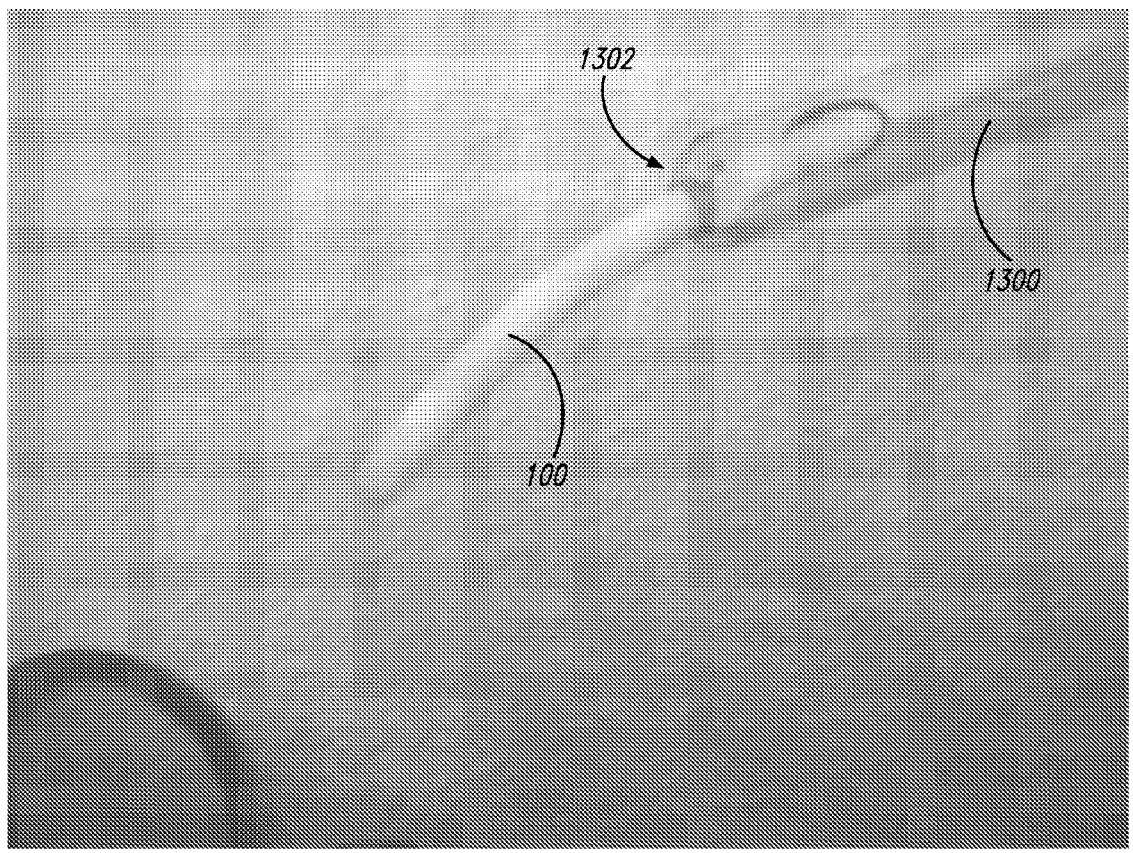

FIG. 13 shows a perspective view of an intubation-tube placement device 100 internal to a modified intubation tube 1300.

Figure 14:
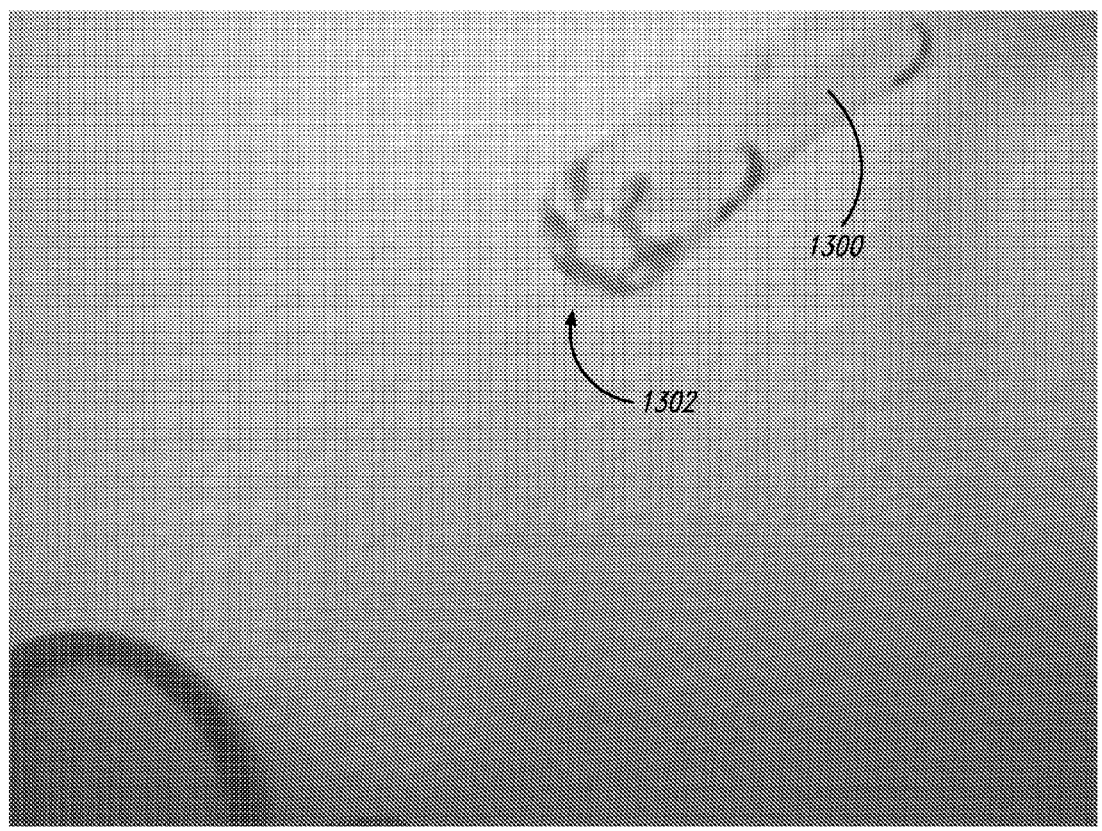

FIG. 14 depicts a perspective isolation view of the rounded tip 1302 of the intubation tube 1300.

Figure 15:
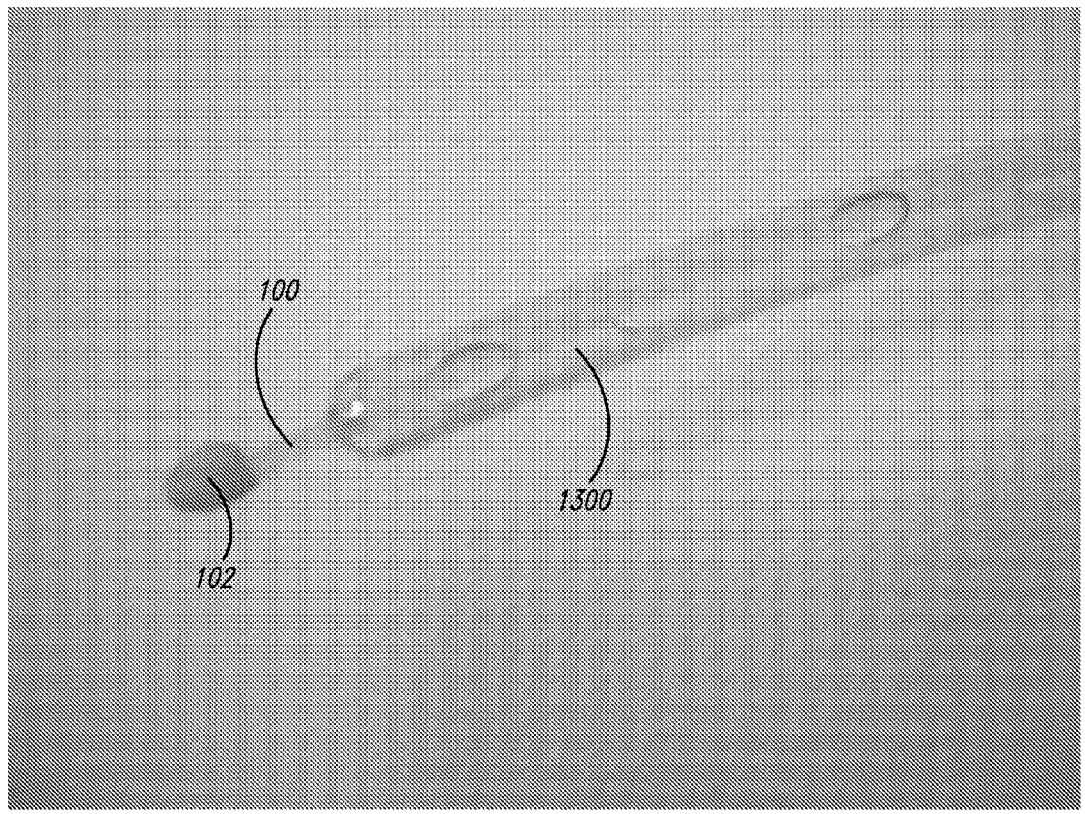

FIG. 15 illustrates a perspective view of an intubation-tube placement device 100 internal to a modified intubation tube 1300.

Figure 16:
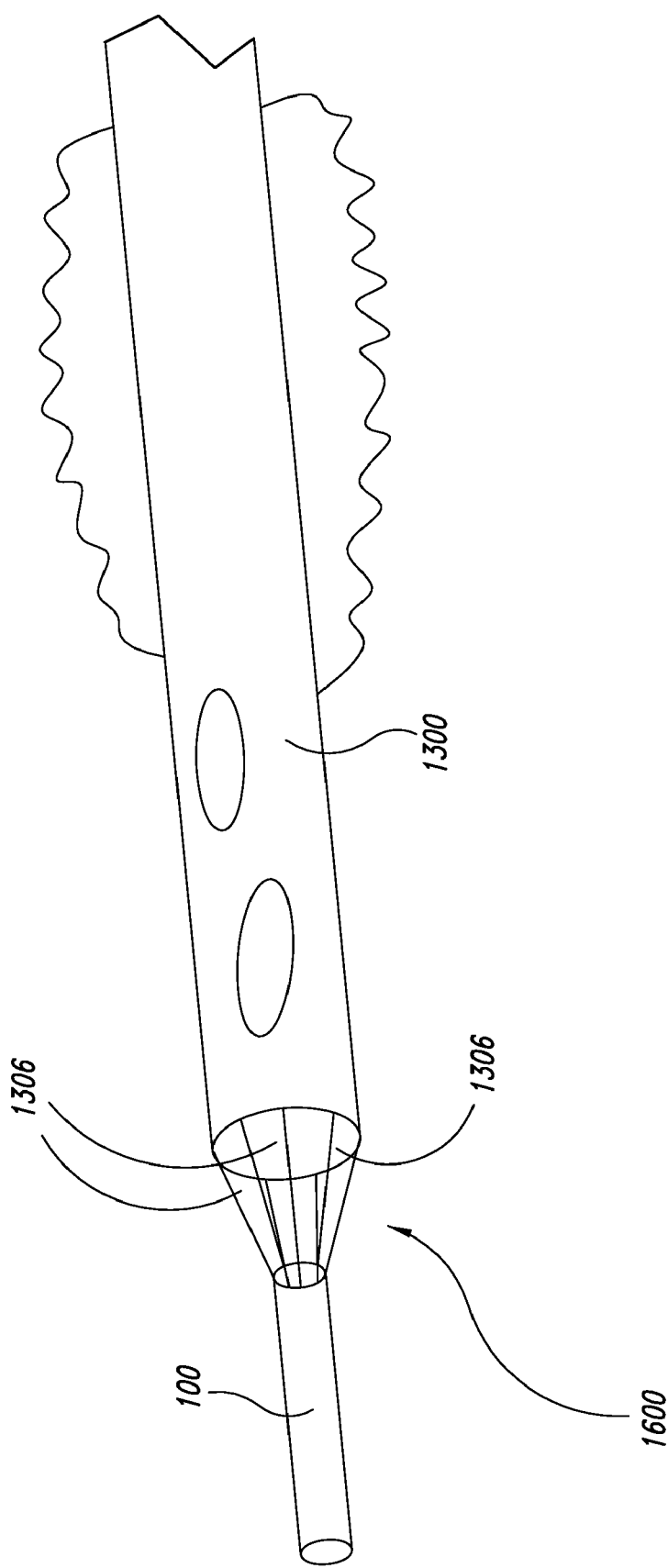

FIG. 16 shows a perspective isolation view of an alternate implementation of the modified intubation tube 1300.

Figure 12A:
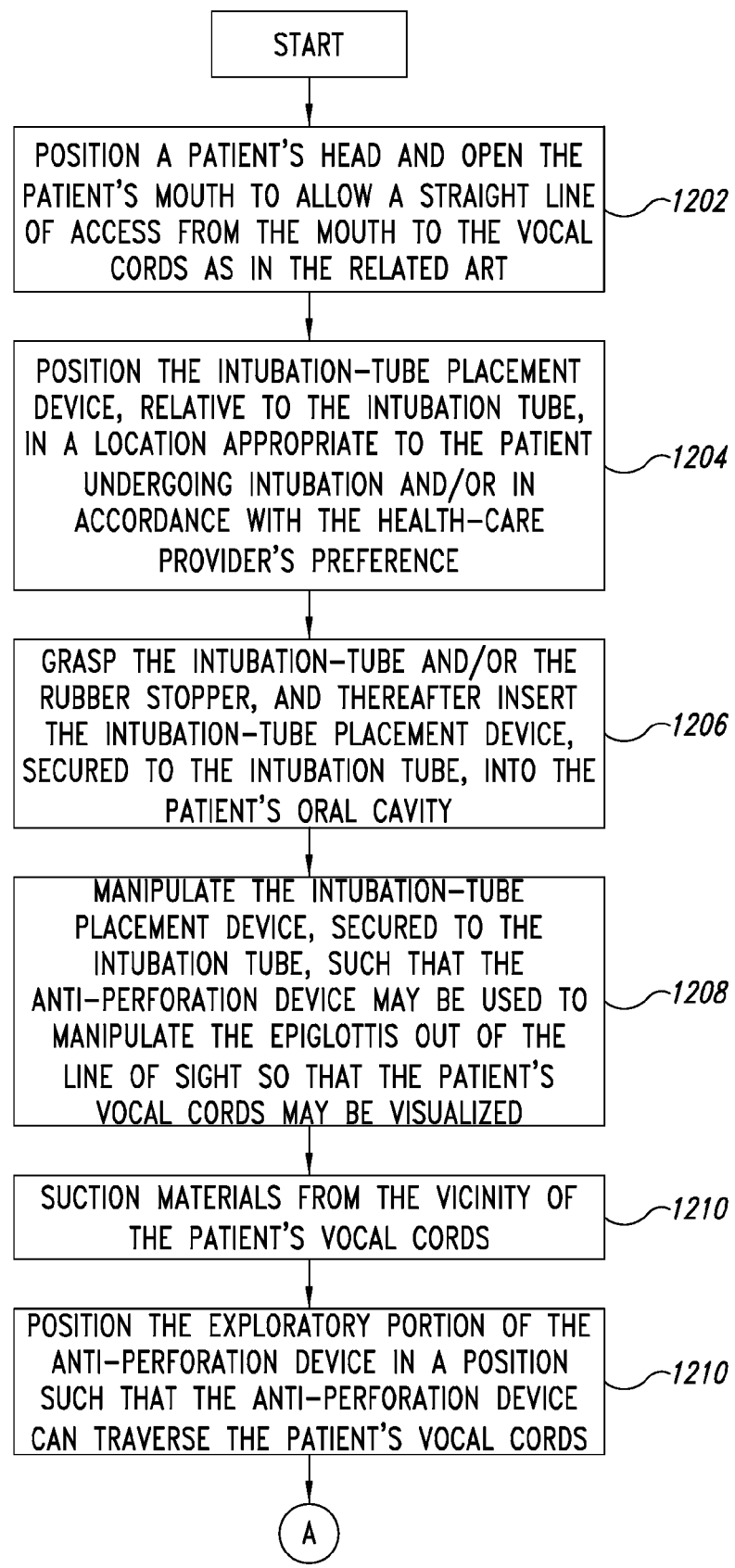
Figure 12B:
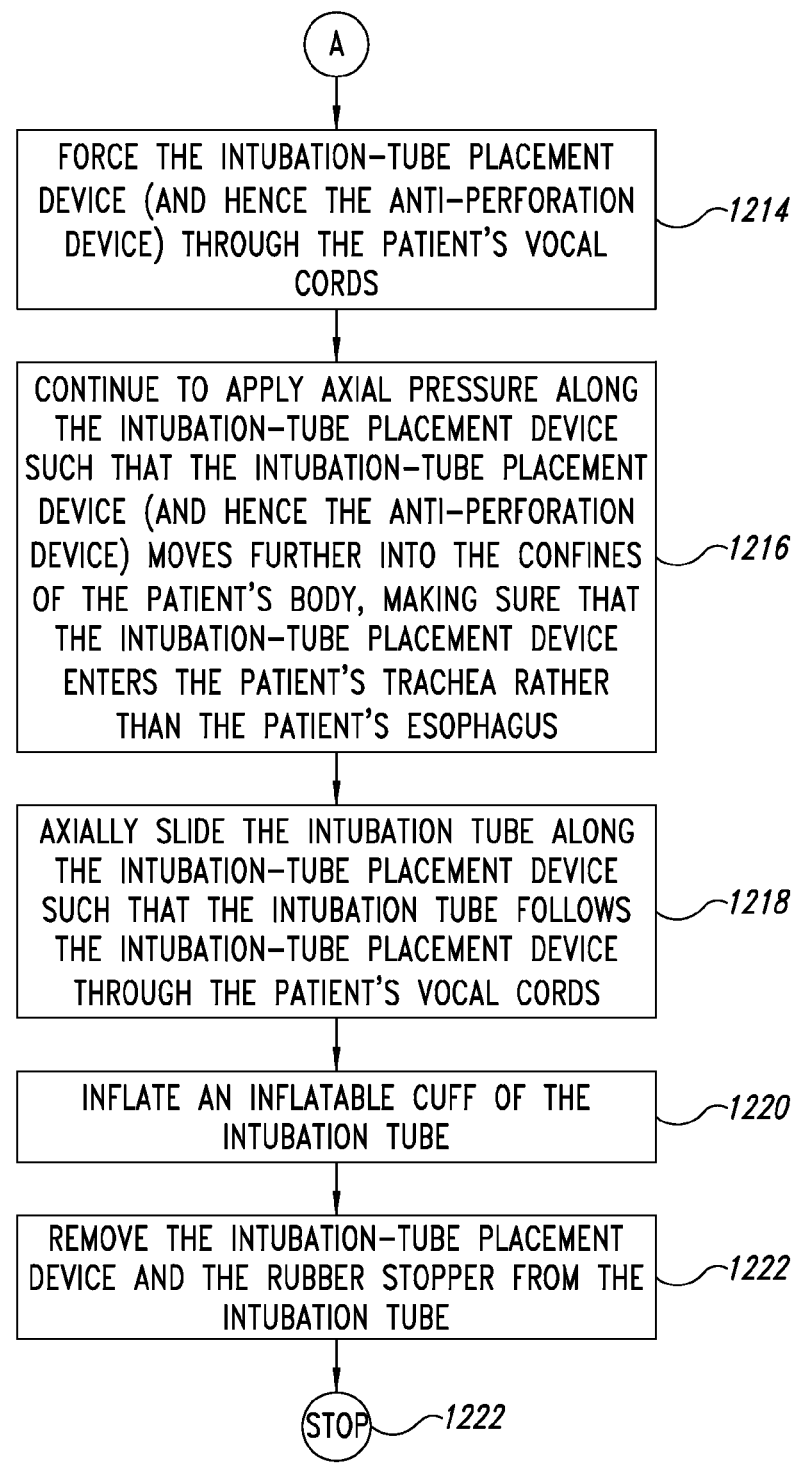

FIG. 12 shows a high-level logic flowchart depicting a process which illustrates how various of the foregoing-described devices may be used.

The use of the same symbols in different drawings typically indicates similar or identical items.

DETAILED DESCRIPTION OF THE INVENTION

Figure 1A:
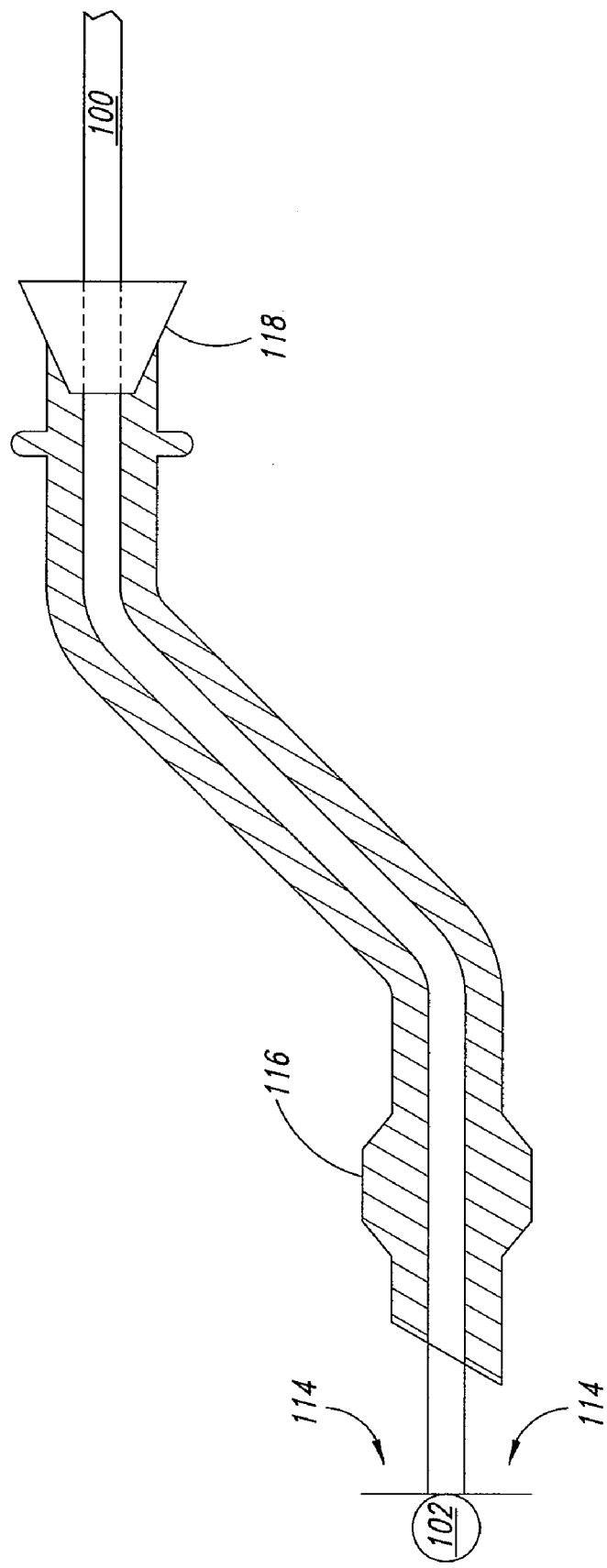

With reference to the figures and with reference now to FIG. 1A, shown is a side-plan view of an intubation-tube placement device 100 secured to an intubation tube 116. In one implementation, the intubation-tube placement device 100 is secured to the intubation tube 116 by a retaining device in contact with the intubation tube 116. Illustrated is that, in one implementation, the retaining device in contact with the intubation tube 116 is characterized by a rubber stopper (or grommet) 118, where the rubber stopper 118 has a hole through which the intubation-tube placement device 100 has been inserted. Shown is that, in one implementation, the rubber stopper 118 is affixed to the intubation tube 116 via mechanical friction, which allows rubber stopper 118 to be severed from the intubation tube 116 via either a simple twisting or pulling motion. That is, in one implementation, the health care provider grasps the intubation tube 116 with one hand, grasps the rubber stopper 118 and intubation-tube placement device 100 with the other hand, and pulls the intubation tube 116 and the rubber stopper 118 in opposite directions such that the rubber stopper 118 breaks away from the intubation tube 116 so that the rubber stopper 118 and the intubation-tube placement device 100 may be removed from the intubation tube 116.

Figure 1B:
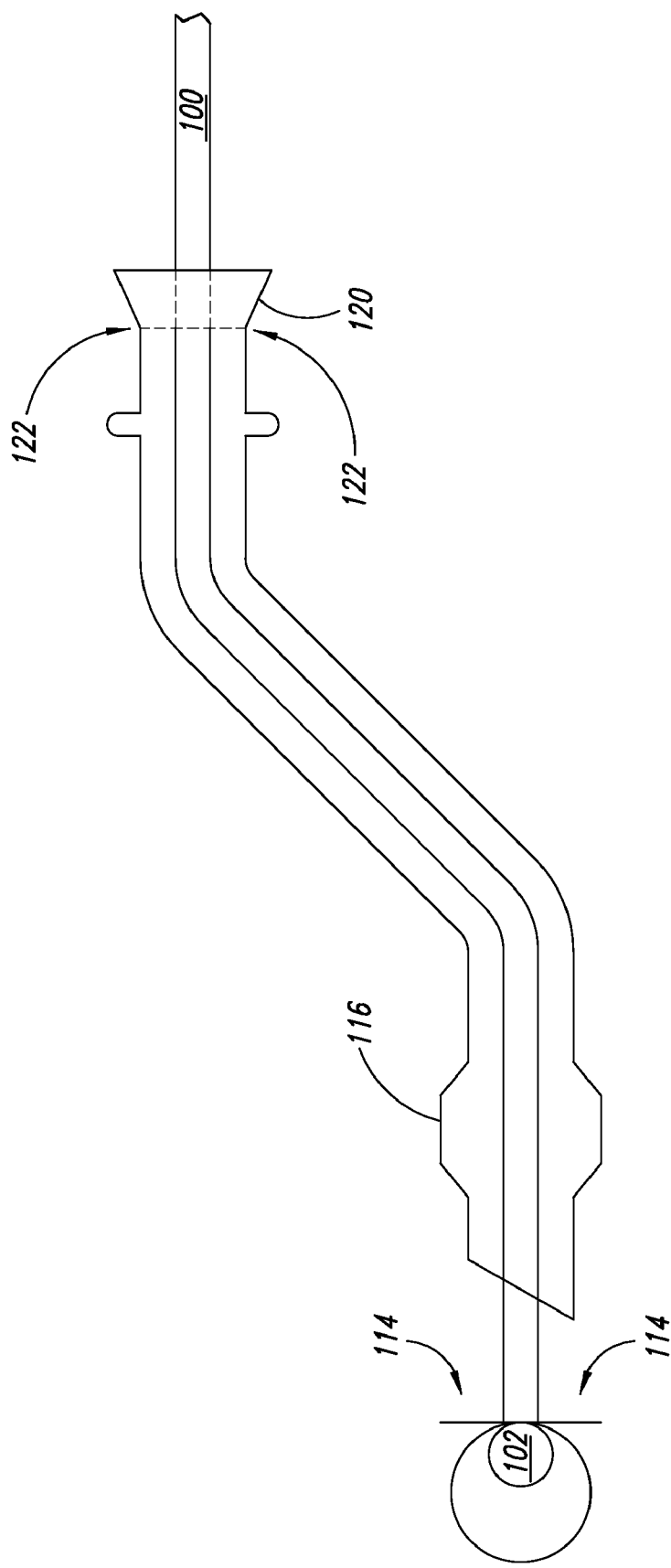

Referring now to FIG. 1B, shown is that another implementation of an intubation-tube placement device 100 secured to an intubation tube 116 is characterized by an intubation-placement-device guide 120 integral with the intubation tube 116, where the intubation-placement-device guide 120 has a hole through which the intubation-tube placement device 100 has been inserted. Illustrated is that, in one implementation, the intubation-placement-device guide 120 is affixed to the intubation tube 116 via a breakaway perforated border 122, which allows the intubation-placement-device guide 120 to be severed from the intubation tube 116 via either a simple twisting or pulling motion. That is, in one implementation, the health care provider grasps the intubation tube 116 with one hand, grasps the intubation-placement-device guide 120 and the intubation-tube placement device 100 with the other hand, and twists the intubation tube 116 and the intubation-placement-device guide 120 in opposite directions such that the intubation-placement-device guide 120 breaks away from the intubation tube 116 so that the intubation-placement-device guide 120 and the intubation-tube placement device 100 may be removed from the intubation tube 116.

In various implementations, an intubation-tube placement device (e.g., intubation-tube placement device 100) is a semi-rigid structure constructed from a material having a relatively low coefficient of friction, so that the intubation-tube placement device 100 may be relatively easily slid back and forth through the hole of a retaining device (e.g., rubber stopper 118 or intubation-placement-device guide 120). In one implementation, this is achieved by forming the intubation-tube placement device from a medical-grade polymeric material, such as medical-grade polyvinyl chloride (PVC) or medical-grade nylon.

In various implementations, an intubation-tube placement device (e.g., intubation-tube placement device 100) is a semi-rigid structure constructed from a material which is malleable and which has a memory quality sufficient to permit a health care provider to manipulate the intubation-tube placement device into a shape or form according to the health care provider's preference. The material is malleable enough to allow the health care provider to relatively easily bend the intubation-tube placement device, and the memory quality is such that, subsequent to the health care provider's bending the intubation tube placement device into any particular shape, the intubation-tube placement device will tend to maintain both itself and an intubation tube (e.g., intubation tube 116), to which the intubation-tube placement device is secured, during use of the intubation-tube-placement device secured to the intubation tube. The inventor believes that health care providers will find such construction particularly attractive in that such health care providers can easily personalize the device to their use preferences. In one implementation, this is achieved by forming the intubation-tube placement device from a medical-grade, reinforced, polymeric material, such as medical-grade reinforced polyvinyl chloride (PVC) or medical-grade reinforced nylon. However, those skilled in the art will appreciate that other materials may be found suitable via a reasonable amount of experimentation in light of the teachings herein.

In various implementations, an intubation-tube placement device (e.g., intubation-tube placement device 100) is a semi-rigid structure having either a cross section appropriate to an adult or a cross section appropriate to a child. In one implementation, the cross section appropriate to a neonatal premature infant is a cross section whose widest point is no greater than 0.05 ("point zero five") mm. In another implementation, the cross section appropriate to a child is a cross section whose widest point is no greater than 0.5 ("point five") mm. In another implementation, the cross section appropriate to an adult is a cross section whose widest point is no greater than 6.0 ("six point zero") mm. In another implementation, the intubation-tube placement device (e.g., intubation-tube placement device 100) is a semi-rigid structure having a cross section appropriate to a veterinary animal (e.g., a horse, a cow, a monkey, a dog, a guinea pig, a mouse, a rat, etc.). In one implementation, the cross section appropriate to a veterinary animal is a cross section whose widest point is no greater than 10.0 ("ten point zero") mm. Those skilled in the art will recognize that the cross sections listed herein are merely exemplary and that many other cross sections can be used dependent upon the patient undergoing intubation and health care provider preference.

As shown herein, the intubation-tube placement device is depicted as a cylindrically-shaped rod. Those having ordinary skill in the art will appreciate that the intubation tube placement device can have many other shapes such as an octagonal shape, an ellipsoid shape, or a square shape.

With reference now again to FIGS. 1A and 1B, illustrated is that an anti-perforation device 102 is coupled to an intubation-tube placement device 100. In one implementation, the anti-perforation device 102 is characterized by an internal light source, which aids the health care provider in placing the intubation-tube placement device 100 (e.g., by illuminating the vocal cords of a patient); in one implementation, the internal light source contains its power source, while in another implementation it is powered via an externalized battery pack via wires (not shown) running through the length of the intubation-tube placement device 100. In another implementation, the anti-perforation device 102 is characterized by a channel which articulates with a channel of the intubation-tube placement device 100 whereby suction can be applied via the anti-perforation device 102. For example, in one implementation, the anti-perforation device 102 has a hole drilled all the way through it, and the intubation-tube placement device 100 is a hollow tube; the anti-perforation device 102 is affixed to the intubation-tube placement device 100 such that the hole aligns with the hollow tube, thereby forming one continuous channel which will support a vacuum and thus allow the health care provider to apply suction through the anti-perforation device 102. With respect to the aspect of suctioning, in another implementation, the intubation-tube placement device 100 forms a hollow tube, and there is no anti-perforation device 102 is coupled to the intubation tube placement device, in which case suction is directly applied via an open end of the hollow tube formed by the intubation-tube placement device 100.

Continuing to refer to FIGS. 1A and 1B, shown is that, in one implementation, tactile-accentuator flaps 114 are coupled to intubation-tube placement device 100. Illustrated is that, in one implementation, each of the tactile-accentuator flaps 114 forms a non-zero angle with an axis of the intubation-tube placement device 100 (e.g., a 90 degree angle such as is shown in FIGS. 1A and 1B). In one embodiment, the tactile-accentuator flaps 114 are affixed to a ring-like structure encompassing the intubation-tube placement device 100. In another embodiment, the tactile-accentuator flaps 114 are directly affixed to the anti-perforation device 102. The inventor points out that while tactile-accentuator flaps 114 are illustrated herein as extending from the body of the intubation-tube placement device 100 and beyond the outermost portions of the anti-perforation device 102, in other contemplated embodiments the tactile-accentuator flaps 114 extend no further from the body of the intubation-tube placement device (100) than the outermost portions of the anti-perforation device 100, thereby allowing the health care provider a more clear line of sight to the patient's vocal cords.

The inventor has found that the retaining device (e.g. rubber stopper 118 or intubation-placement-device guide 120) serves as a "handle" for the intubation-tube placement device 100. That is, the inventor has found that the retaining device "amplifies" the physical motion of the proximate end (e.g., the end to which the anti-perforation device 102 is affixed) of the intubation-tube placement device 100, making it easier to intubate a patient in the absence of the handle. In addition, while the retaining device is treated as the handle for the sake of illustration herein, in another contemplated embodiment, a handle is actually affixed to the intubation-tube placement device 100, while in another contemplated embodiment the handle is actually affixed to the intubation tube 116.

Referring now to FIG. 2, depicted is a side-plan isolation view of an anti-perforation device 102 coupled to an intubation-tube placement device 100. Illustrated is that, in one implementation, the anti-perforation device 102 is characterized by the light source internal to the anti-perforation device 102 (illustrated in FIG. 2 via light rays emanating from the anti-perforation device 102). Shown is that the anti-perforation device 102 has a trailing portion 104 and an exploratory portion 106. Depicted is that, in one implementation, the exploratory portion 106 of the anti-perforation device 102 has a spheroid shape, where lines drawn tangent to the spheroid shape would typically form an oblique angle with the axis of the intubation-tube placement device 100. Further depicted is that, in one implementation, a portion of the spheroid shape extends beyond the outer diameter of the intubation-tube placement device 100, which the inventor has found particularly advantageous in preventing perforation of internal body structures. In one implementation, the spheroid shape proves particularly advantageous in that it serves to protect the internal structures of a patient undergoing intubation.

With reference now to FIG. 3A, shown is a side-plan isolation view of an alternate embodiment of an anti-perforation device 102 coupled to an intubation-tube placement device 100. Depicted is an open channel 300 between the trailing portion 104 and the exploratory portion 106 of the anti-perforation device 102. Illustrated is that, in one implementation, the intubation-tube placement device 100 forms a hollow tube. Shown is that the trailing portion 104 of the anti-perforation device 102 is coupled to the intubation-tube placement device 100 such that the channel 300 of the anti-perforation device 102 substantially aligns with the hollow tube formed by the intubation-tube placement device 100, thereby forming a suctioning tube. Depicted is that, in one implementation, the exploratory portion 106 of the anti-perforation device 102 has a ellipsoid shape, where lines drawn tangent to the ellipsoid shape would typically form an oblique angle with the axis of the intubation-tube placement device 100. Further depicted is that, in one implementation, a portion of the ellipsoid shape extends beyond the outer diameter of the intubation-tube placement device 100, which the inventor has found particularly advantageous in preventing perforation of internal body structures.

Referring now to FIG. 3B, depicted is a side-plan isolation view of an alternate embodiment of an anti-perforation device 102 coupled to an intubation-tube placement device 100. Illustrated is an open channel 300 between the trailing portion 104 and the exploratory portion 106 of the anti-perforation device 102. Shown is that, in one implementation, the intubation-tube placement device 100 forms a hollow tube.

Depicted is that the trailing portion 104 of the anti-perforation device 102 is coupled to the intubation-tube placement device 100 such that the channel 300 of the anti-perforation device 102 substantially aligns with the hollow tube formed by the intubation-tube placement device 100, thereby forming a suctioning tube. Depicted is that, in one implementation, the exploratory portion 106 of the anti-perforation device 102 has a spheroid shape, where lines drawn tangent to the spheroid shape would typically form an oblique angle with the axis of the intubation-tube placement device 100. Further depicted is that, in one implementation, a portion of the spheroid shape extends beyond the outer diameter of the intubation-tube placement device 100, which the inventor has found particularly advantageous in preventing perforation of internal body structures.

With reference now to FIG. 3C, illustrated is a side-plan isolation view of an alternate embodiment of an anti-perforation device 102 coupled to an intubation-tube placement device 100. Shown is that, in one implementation, the anti-perforation device 102 has a spheroid shape formed from solid surfaces arranged in various angles. Depicted is that, in one implementation, the exploratory portion 106 of the anti-perforation device 102 has an angled shape, where lines drawn tangent to the angled shape would typically form an oblique angle with the axis of the intubation-tube placement device 100. Further depicted is that, in one implementation, a portion of the angled shape extends beyond the outer diameter of the intubation-tube placement device 100, which the inventor has found particularly advantageous in preventing perforation of internal body structures.

While the exploratory portion 106 of the anti-perforation device 102 has been shown in FIGS. 2-3C as having a fixed structure, in one contemplated embodiment the exploratory portion 106 of the anti-perforation device 102 is formed from a medical-grade room-temperature malleable material (e.g., a medical-grade polymer or wax) which can be manipulated into a shape chosen by the health care provider performing intubation. For example, the anti-perforation device 102 could come prepackaged in a spherical shape, which the health care provider could then manipulate as he sees fit. In addition, in one contemplated embodiment the anti-perforation device 102 comes prepackaged with a lubricant coating the anti-perforation device 102.

Referring now to FIG. 4A, shown is a front-plan view of an anti-perforation device 102 coupled to an intubation-tube placement device 100. Depicted is that, in one implementation, the intubation-tube placement device 100 has a cylindrical shape. In one implementation, the intubation-tube placement device 100 forms a hollow tube, while in another implementation, the intubation-tube placement device 100 forms a solid rod.

With reference now to FIG. 4B, depicted is a front-plan view of an anti-perforation device 102 coupled to an intubation-tube placement device 100. Illustrated is that, in one implementation, the intubation-tube placement device 100 has an octagonal shape. In one implementation, the intubation-tube placement device 100 forms a hollow tube, while in another implementation, the intubation-tube placement device 100 forms a solid rod.

Referring now to FIG. 5, shown is a side-plan view of tactile-accentuator flaps 114 coupled to an intubation-tube placement device 100. Illustrated is that, in one implementation, each of the tactile-accentuator flaps 114 forms a non-zero angle with an axis of the intubation-tube placement device 100. Shown is that, in one implementation, the tactile-accentuator flaps 114 are affixed to a ring-like structure 116 encompassing the intubation-tube placement device 100. Depicted is that, in one implementation, the tactile-accentuator flaps 114 are proximate to the anti-perforation device 102, which is itself coupled to the intubation-tube placement device 100. In another implementation, not shown, the tactile-accentuator flaps 114 are directly coupled to the anti-perforation device 102.

With reference now to FIG. 6A, depicted is a side-plan isolation view of an alternate implementation of tactile-accentuator flaps 114 coupled to an intubation-tube placement device 100. Illustrated is that, in one implementation, each of the tactile-accentuator flaps 114 forms a non-zero angle with an axis of the intubation-tube placement device 100. Shown is that, in one implementation, the tactile-accentuator flaps 114 are affixed to a ring-like structure 116 encompassing the intubation-tube placement device 100. Depicted is that, in one implementation, the tactile-accentuator flaps 114 are proximate to the anti-perforation device 102 coupled to the intubation-tube placement device 100. In another implementation, not shown, the tactile-accentuator flaps 114 are directly coupled to the anti-perforation device 102.

Referring now to FIG. 6B, illustrated is a side-plan isolation view of an alternate implementation of tactile-accentuator flaps 114 coupled to an intubation-tube placement device 100. Shown is that, in one implementation, each of the tactile-accentuator flaps 114 forms a non-zero angle with an axis of the intubation-tube placement device 100. Depicted is that, in one implementation, the tactile-accentuator flaps 114 are directly affixed to the anti-perforation device 102. Illustrated is that, in one implementation, the tactile-accentuator flaps 114 are proximate to the anti-perforation device 102 coupled to the intubation-tube placement device 100. In another implementation, not shown, the tactile-accentuator flaps 114 are directly coupled to the intubation-tube placement device 100.

With reference data FIG. 6C, shown is a side-plan isolation view of an alternate implementation of tactile-accentuator flaps 114 coupled to an intubation-tube placement device 100. Shown is that, in one implementation, each of the tactile-accentuator flaps 114 forms a non-zero angle with an axis of the intubation-tube placement device 100. Depicted is that, in one implementation, the tactile-accentuator flaps 114 are directly affixed to the anti-perforation device 102. Illustrated is that, in one implementation, the tactile-accentuator flaps 114 are proximate to the anti-perforation device 102 coupled to the intubation-tube placement device 100. In another implementation, not shown, the tactile-accentuator flaps 114 are directly coupled to the intubation-tube placement device 100.

In various implementations, a tactile-accentuator flap (e.g., one of the tactile-accentuator flaps 114) is a semi-rigid structure constructed from a material having a relatively low coefficient of friction, so that the tactile-accentuator flaps may be relatively easily slid back and forth across the internal structures of the body (e.g., the cartilaginous rings lining the trachea of an animal). In one implementation, this is achieved by forming the tactile-accentuator flap from a medical-grade polymeric material, such as medical-grade polyvinyl chloride (PVC) or medical-grade nylon. The inventor has discovered that the tactile accentuator flaps are particularly useful in performing intubations in that the tactile accentuator flaps allow the intubating health-care provider to detect the cartilaginous rings lining the trachea, by amplifying the tactile impressions generated by such cartilaginous rings. The inventor has discovered that such tactile amplification increases the likelihood that an intubation tube will be placed in the trachea of a patient rather than the esophagus of the patient.

Referring now to FIGS. 7A and 7B, shown are structures substantially analogous to those depicted in FIGS. 4A and 4B, to which have been affixed tactile-accentuator flaps 114. Depicted is that, in one implementation, each of the tactile-accentuator flaps 114 presents in front-plan view as having a 1 mm by 1 mm facial profile. The inventor has found that it is advantageous that the tactile-accentuator flaps 114 be thin enough to permit flexing and bending in their profiles; exactly how thin the tactile-accentuator flaps 114 will be will vary in application dependent upon the materials used and can be determined empirically via a reasonable amount of experimentation. However, while various sizes and shapes of the tactile-accentuator flaps 114 have been illustrated and described herein, those skilled in the art will appreciate that other sizes and shapes of facial profiles can be utilized in light of the teachings herein via a minimal amount of experimentation.

Those skilled in the art will appreciate that while FIGS. 5-7B depict only two tactile-accentuator flaps 114, the teachings herein are not limited to only two flaps and that other numbers of tactile-accentuator flaps 114 are possible (e.g., one, three, four, five, etc.).

Figure 8:
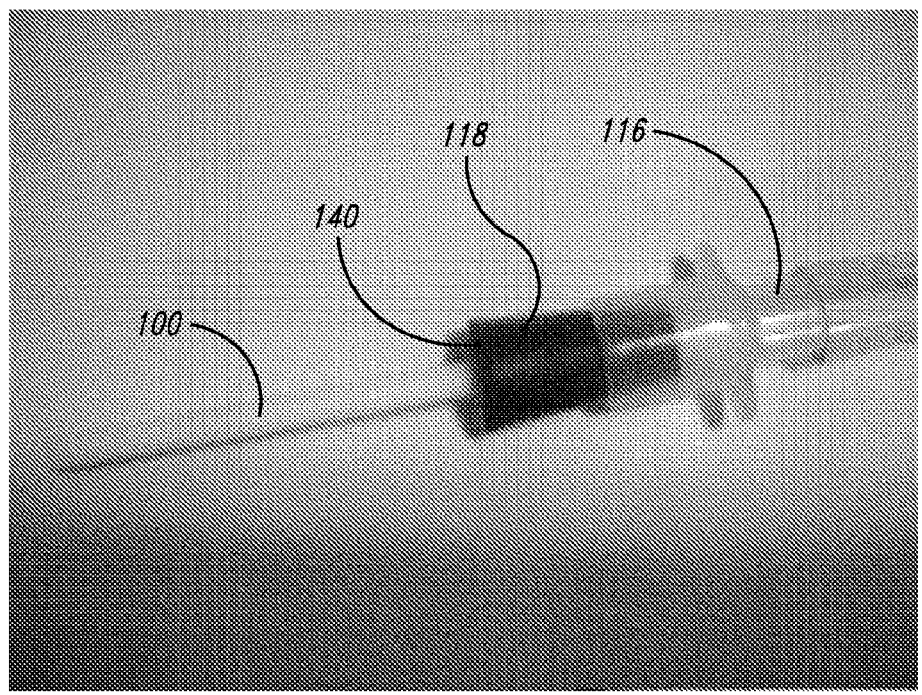
FIG. 8 depicts an isolated perspective view of an intubation-tube placement device 100 secured to an intubation tube 116.

With reference now to FIG. 8, depicted is an isolated perspective view of an intubation-tube placement device 100 secured to an intubation tube 116. Illustrated is the intubation-tube placement device 100 held internal to the intubation tube 116 via a retaining device in contact with the intubation tube 116. Shown is that, in one implementation, the retaining device is a rubber stopper 118 having a hole 140, which runs the length of the rubber stopper 118, through which intubation-tube placement device 100 has been inserted. Depicted is that, in one implementation, the rubber stopper 118 holds the intubation-tube placement device 100 internal to the intubation tube 116 via mechanical friction.

Referring now to FIG. 9, shown is a perspective view of an intubation tube 116, an intubation-tube placement device 100, and a rubber stopper 118 in disassembled form.

With reference now to FIG. 10, depicted is a top-plan view of three different-sized implementations of a rubber stopper 118, and an intubation-tube placement device 100. As has been described, varying sizes of the intubation-tube placement device 100 can be used depending upon the needs of the patient undergoing intubation and/or preferences of the health-care provider performing intubation.

Referring now to FIG. 11, illustrated is a side-plan view of an intubation-tube placement device 100 internal to intubation tube 116. Shown is that the intubation-tube placement device 100 has coupled to it an implementation of the anti-perforation device 120.

With reference now to FIG. 13, shown is a perspective view of an intubation-tube placement device 100 internal to a modified intubation tube 1300. Shown is the modified intubation tube 1300 has a rounded tip 1302, which is different from the beveled tip of intubation tube 116. The inventor has empirically determined that the rounded tip 1302 of the intubation tube 1300 is particularly advantageous.

Referring now to FIG. 14, depicted is a perspective isolation view of the rounded tip 1302 of the intubation tube 1300.

With reference now to FIG. 15, illustrated is a perspective view of an intubation-tube placement device 100 internal to a modified intubation tube 1300. Shown coupled to intubation-tube placement device 100 is an implementation of an anti-perforation device 102.

Referring now to FIG. 16, shown is a perspective isolation view of an alternate implementation of the modified intubation tube 1300. Depicted is a rounded and tapered tip 1600 having open slots, or ports, 1306 which allow for ventilation of an intubated patient.

Although not explicitly shown, it is to be understood that in most implementations the modified intubation tube 1300 will have inflatable cuffs on them to allow proper oxygenation and ventilation of intubated patients.

Those having ordinary skill in the art will recognize that national hospital accreditation standards have recently prohibited intubation (e.g., endotracheal) tubes from being opened before use. The practical effect of such standards is that now that all health care providers performing intubation must first open a medical-grade sterile package, insert a metal stylet into the endotracheal tube, and bend both to the desired shape before intubating. Accordingly, in one implementation an intubation-tube placement device 100 secured to an intubation tube 116 comes pre-packaged, as a unit, in a medical-grade sterile package. This is particularly attractive over the related art in that that when the intubation-tube placement device 100 secured to an intubation tube 116 is removed from its packaging it is substantially immediately ready to be used. That is, the intubation-tube placement device 100 secured to an intubation tube 116, prepackaged as a unit in medical-grade sterile packaging, has the advantage of saving time from having to load it.

The foregoing has described various devices. Following is a description of one method implementation which illustrates how several of the foregoing-described various devices may be used.

With reference now to FIG. 12, shown is a high-level logic flowchart depicting a process which illustrates how various of the foregoing-described devices may be used. Those skilled in the art will recognize that the uses depicted and/or described are merely illustrative, and are not exhaustive.

Referring now to FIG. 12 and FIG. 1A, method step 1200 depicts the start of the process. Method step 1202 illustrates positioning a patient's head and opening the patient's mouth to allow a straight line of access from the mouth to the vocal cords as in the related art (typically with the aid of a lighted laryngoscope). Method step 1204 shows the health-care provider positioning the intubation-tube placement device 100, relative to the intubation tube 116, in a location appropriate to the patient undergoing intubation and/or in accordance with the health-care provider's preference; in one implementation, this is achieved via the health-care provider grasping the intubation tube 116 and/or the rubber stopper 118 with one hand and manipulating the intubation-tube placement device with the other hand until the anti-perforation device 102 extends from the intubation tube 116 at a distance which the health-care provider deems appropriate (e.g., extending 5 cm from the intubation tube for neonates or extending 20 cm from the intubation tube for average-sized adults).

Method step 1206 depicts the health-care provider grasping the intubation tube 116 and/or the rubber stopper 118, and thereafter inserting the intubation-tube placement device 100, secured to the intubation tube 116, into the patient's oral cavity. Method step 1208 illustrates the health-care provider manipulating the intubation-tube placement device 100, secured to the intubation tube 116, such that the anti-perforation device 102 may be used to manipulate the epiglottis out of the line of sight so that the patient's vocal cords may be visualized where standard laryngoscope manipulation fails to reveal the cords. Additionally, when the vocal cords are not otherwise able to be visualized through laryngoscope or the device described herein's manipulation, the exploratory portion of the device can be gently advanced as anterior as possible to the posterior aspect of the visualized epiglottis or where the health-care provider best believes the epiglottis to be to facilitate insertion within the trachea. The device's design allows for endotracheal placement interpretation by allowing the healthcare provider to appreciate either the cartilaginous rings lining the trachea through tactile stimulus or until hang-up of the device (usually at the bifurcation of the trachea) is experienced strongly suggesting endotracheal intubation; in one implementation, the light source internal to the anti-perforation device 102 aids the health-care provider in this process. One advantage to this one implementation of the light source is the ability of the health-care provider to otherwise dispense with the necessary reliance upon an expensive lighted laryngoscope and the accompanying supportive costs to maintain laryngoscopes (sterilization, changing light bulbs, incompatible blades, bulbs, etc). This implementation allows for as many intubations as there are devices for without reliance upon sterilizing procedures or other costly supportive maintenance. In addition to the foregoing, the inventor has found that one particularly advantageous use of the structures described herein is that the intubation-tube placement device 100 having anti-perforation device 102 and/or tactile-accentuator rings 114 allows for blind placement without any light source. or use of even a laryngoscope blade, by simply using the health-care provider's fingers to first identify the position of the epiglottis and then to slide the exploratory portion of the device as anterior as possible again to the posterior aspect of the epiglottis to facilitate endotracheal intubation until tactile confirmation suggests endotracheal intubation. In one use, the endotracheal intubation is confirmed through bagging and other standard confirmatory techniques. The inventor points out that the foregoing-described blind intubation may be very attractive where a health-care provider may want to otherwise intubate a patient under low lighting or unfavorable conditions such as out in the pre-hospital setting or in a combat area.

Method step 1210 depicts the optional step of suctioning materials from the vicinity of the patient's vocal cords; in one implementation, the foregoing is achieved via the trailing portion 104 of the anti-perforation device 102 coupled to the intubation-tube placement device 100 such that the channel 300 of the anti-perforation device 102 substantially aligns with the hollow tube formed by the intubation-tube placement device 100, thereby forming a suctioning tube (e.g., see FIGS. 3A and 3B).

Method step 1212 shows the step of the health-care provider positioning the exploratory portion 106 of the anti-perforation device 102 in a position such that the anti-perforation device 102 can traverse the patient's vocal cords; in one implementation, the health-care provider is aided in this task of positioning in that the intubation-tube placement device 100 secured to the intubation tube 116 serves as a "handle" for the intubation-tube placement device 100, where the "handle" tends to "amplify" the movements of the health-care provider's fingers to allow for very accurate positioning of the intubation-tube placement device 100 (and hence the anti-perforation device 102) within the patient's oral cavity.

Method step 1214 depicts the step of the health-care provider forcing the intubation-tube placement device 100 (and hence the anti-perforation device 102) through the patient's vocal cords; in one implementation, the foregoing is achieved via the health-care provider grasping the intubation-tube placement device 100 near the rubber stopper 118, and applying pressure along the axis of the intubation-tube placement device 100 such that the intubation-tube placement device 100 slides axially within the hole of the rubber stopper 118 such that the exploratory surface 106 of the anti-perforation device 102 pushes aside the patient's vocal cords.

Method step 1216 illustrates the step of the health-care provider continuing to apply axial pressure along the intubation-tube placement device 100 such that the intubation-tube placement device 100 (and hence the anti-perforation device 102) moves further into the confines of the patient's body, making sure that the intubation-tube placement device 100 enters the patient's trachea rather than the patient's esophagus; in one implementation, the health-care provider is aided in the foregoing-described endeavor by the tactile-accentuator flaps 114, in that various of the tactile-accentuator flaps 114 impact upon the cartilaginous rings lining the trachea, and mechanically transmit such impact, back through the intubation-tube placement device 100, such that the health-care provider performing the intubation can be substantially assured that he has placed the intubation-tube placement device 100 in the trachea rather than in the esophagus.

Method step 1218 shows the step of the health-care provider axially sliding the intubation tube 116 along the intubation-tube placement device 100 such that the intubation tube 116 follows the intubation-tube placement device 100 through the patient's vocal cords; in one implementation, this is achieved via the health-care provider grasping the intubation-tube placement device 100 and sliding the rubber stopper 118 axially along the intubation-tube placement device 100 such that the intubation tube 116 clears the patient's vocal cords.

Method step 1220 depicts the step of the health-care provider inflating an inflatable cuff of the intubation tube 116, as in the related art.

Thereafter, method step 1222 illustrates the step of the health-care provider removing the intubation-tube placement device 100 and the rubber stopper 118 from the intubation tube 116; in one implementation, this is achieved via the health-care provider simultaneously grasping the intubation-tube placement device 100 and the rubber stopper 118, and pulling the intubation-tube placement device 100 and the rubber stopper 118 from the intubation tube 116. Method step 1224 shows the end of the process.

As noted in the provisional patent application, filed Mar. 5, 2001, and hereby incorporated by reference, in its entirety, in the present detailed description, the methods and devices described herein differ from the related-art use of the Eschmann stylet in several ways. For example, the related-art Eschmann stylet does not have an anti-perforation device, such as has been described herein, and, in fact, the present inventor has observed the Eschmann stylet perforating body tissues (e.g., a tumor) during use. The anti-perforation device described herein decreases the likelihood that such perforation will occur and hence provides an advantage over the related-art Eschmann stylet. In addition, in use, a health-care provider first passes the related-art Eschmann stylet through a patient's vocal cords, and thereafter the health-care provider introduces the endotracheal tube over the Eschmann stylet, in through the patient's vocal cords into the patient's trachea. The inventor points out that, according to the Eschmann stylet's manufacturer's recommendation it is intended as a rescue device and only for use only after failed conventional laryngoscopy, whereas the herein described one unit assembly design (i.e., the intubation-tube placement device 100 secured to the intubation tube 116) permits attempted intubation during all scenarios—a characteristic feature not known to any other device. In contrast, the intubation-tube placement device secured to an intubation tube, such as has been described herein, is used differently in that it allows the intubation-tube placement device secured to the intubation tube to be placed as a unit, thereby increasing the speed and ease of intubation over the related-art use of the Eschmann stylet. The inventor has found empirically that the one unit assembly character of the intubation-tube placement device 100 secured to the intubation tube 116, described herein, provides a much larger surface area to be held by the health-care provider thereby greatly improving their ability to control the device and improve the success rate of intubations. The inventor has found empirically that the Eschmann stylet's surface area held by the health-care provider is considerably smaller and therefore more difficult to grasp and more importantly control with control being a critical feature during any attempted life saving procedure. Additionally, the inventor has found empirically that the Eschmann stylet's resin-coated exterior is very susceptible to cracking and flaking which can lead to foreign objects being aspirated into the bronchial airway system and to be a site for foreign debris to be retained. The inventor also points out that the Eschmann stylet is not intended to be a disposable item (as are most implementations described herein), and that the Eschmann stylet is costly to produce whereas the devices described herein is, in most implementations, entirely disposable and therefore not reliant upon a sterilizing process before use.

In addition, the methods and devices described herein differ from the related-art lighted wand technique in several ways. For example, the related-art lighted wand technique uses an intense light to trans-illuminate a patient's laryngeal structures internally which can be seen from the exterior of a patient's body to place an endotracheal tube. In contrast, the methods and devices described herein allow for placement of the endotracheal tube either blindly or by direct visual inspection of the interior of the patient's mouth and vocal cords, and light source described herein facilitates such placement by direct visual inspection.

In addition, the methods and devices described herein differ from the related-art devices and techniques in that none of the related-art devices and techniques used tactile-accentuator flaps to detect the cartilaginous rings of the patient's trachea, nor do the related-art devices and techniques provide for suction via the use of an intubation-tube placement device such as has been described herein.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

For example, although the tactile-accentuator flaps have been described herein in the context of a specifically-crafted intubation-tube placement device, it is to be understood that such tactile-accentuator flaps would also have utility when used with other devices utilized to place intubation tubes (e.g., the Eschmann stylet, fiber optic scopes, bronchoscopes, etc.). As another example, although the specifically-crafted intubation-tube placement device secured to an intubation tube has been described herein, it is to be understood that the foregoing-described structure would also have utility when used with other devices utilized to place intubation tubes (e.g. the Eschmann stylet, the lightwand, fiber optic intubating scopes, etc.).

Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

The invention claimed is:

1. A method comprising:
   removably securing a proximal end of an intubation-tube placement device to a proximal end of an intubation tube with a stopper such that the placement device extends through the intubation tube and a tactile accentuator flap at a distal end of the placement device extends out of a distal end of the intubation tube;
   inserting the distal end of the intubation-tube placement device into a patient's oral cavity;
   detecting cartilaginous rings of a trachea via the tactile-accentuator flap;
   forcing the distal end of the intubation-tube placement device through the patient's vocal cords; and
   axially sliding the intubation tube along the intubation-tube placement device such that the intubation tube follows the distal end of the intubation-tube placement device through the patient's vocal cords.

2. The method of claim 1, wherein said intubation-tube placement device comprises a light source.

3. The method of claim 1, wherein said forcing the intubation-tube placement device through the patient's vocal cords comprises:
suctioning materials from a vicinity of the patient's vocal cords via a suction tube formed by the intubation-tube placement device.

4. The method of claim 3, wherein the suction tube formed by the intubation-tube placement device comprises:
the intubation-tube placement device forming a hollow tube.

5. The method of claim 3, wherein the suction tube formed by the intubation tube placement device comprises:
the intubation-tube placement device forming a hollow tube;
an anti-perforation device having a trailing portion and an exploratory portion;
a channel between the trailing portion and the exploratory portion of said anti-perforation device; and
the trailing portion coupled to said intubation-tube placement device such that the channel substantially aligns with the hollow tube.

6. The method of claim 1, wherein said forcing the intubation-tube placement device through the patient's vocal cords comprises:
applying axial pressure along the intubation-tube placement device such that the intubation-tube placement device moves into the patient's trachea.

7. The method of claim 1, further comprising:
breaking a perforated border along a portion of the intubation tube.

8. The method of claim 1 wherein,
securing the intubation-tube placement device to the intubation tube comprises inserting the placement device into a hole in the stopper and inserting the stopper into the intubation tube; and
inserting the distal end of the intubation-tube placement device into the patient's oral cavity comprises manipulating the intubation-tube placement device by manipulating the stopper.

9. The method of claim 1 wherein,
securing the intubation-tube placement device to the intubation tube comprises using mechanical friction to hold the placement device in position in the intubation tube.

10. An intubation device, comprising:
an intubation placement device having a bendable distal end configured to be introduced through a set of vocal cords, the distal end of the intubation placement device having a tactile accentuator flap configured to detect cartilaginous rings of the trachea;
an intubation tube having a distal and a proximal end; and
a stopper configured to removably secure a proximal end of the placement device to a proximal end of the intubation tube with the placement device extending inside the intubation tube and the distal end of the placement device extending out of the distal end of the intubation tube.

11. The intubation device of claim 10 wherein the stopper comprises a rubber stopper having a center hole configured to receive the intubation placement device.

12. The intubation device of claim 11 wherein the stopper is configured to be partially received into the intubation tube.

13. The intubation device of claim 10 wherein the intubation placement device comprises a hollow tube.

14. The intubation device of claim 13, further comprising:
a fiber optic cable configured to extend into the intubation placement device.

15. The intubation device of claim 10 wherein the intubation placement device comprises a semi-rigid material.

16. The intubation device of claim 15 wherein the intubation placement device comprises a bendable rod.

17. The intubation device of claim 10 wherein the intubation placement device comprises a medical-grade polymeric material.

18. The intubation device of claim 10 wherein the distal end of the intubation placement device comprises an anti-perforation device.

19. The intubation device of claim 10 wherein the stopper comprises a detachable portion of the proximal end of the intubation tube.

20. The intubation device of claim 19 wherein a border of the detachable portion is perforated.

21. The intubation device of claim 10 wherein the stopper is configured to facilitate positioning of the distal end of the placement device as it is introduced through the set of vocal cords.

22. A method of intubating a patient, comprising:
removably securing a proximal portion of a endotracheal placement device to a proximal end of an intubation tube with a stopper such that the endotracheal placement device extends through the intubation tube and a bendable distal portion of the endotracheal placement device extends out through a distal end of the intubation tube;
subsequently guiding the distal portion of the endotracheal placement device through the patient's vocal cords, the guiding including detecting cartilaginous rings with a tactile accentuator flap coupled to the endotracheal placement device;
guiding the intubation tube through the patient's vocal cords such that the distal end of the intubation tube follows the distal portion of the endotracheal placement device through the patient's vocal cords; and
subsequently pulling the endotracheal placement device out of the intubation tube, leaving the intubation tube in position in the patient.

23. The method of claim 22 wherein subsequently pulling the endotracheal placement device out of the intubation tube comprises twisting the endotracheal placement device and the endotracheal tube in opposite directions to separate the stopper and the endotracheal tube.

24. The method of claim 22 wherein the endotracheal placement device comprises a hollow tube and guiding the endotracheal placement device through the patient's vocal cords comprises:
suctioning materials from a vicinity of the patient's vocal cords.

25. The method of claim 22 wherein the intubation tube comprises a wall, further comprising:
providing a plurality of ventilation holes along the wall in the portion of endotracheal tube that follows the endotracheal placement device.

26. The method of claim 22 wherein pulling the endotracheal placement device out of the intubation tube comprises:
breaking a perforated border adjacent to the proximal portion of the intubation tube.

27. An intubation device, comprising:
an intubation tube having a distal end and a proximal end;
a endotracheal placement device having a semi-rigid distal end configured to pass through vocal cords and into a trachea and a tactile accentuator flap configured to detect cartilaginous rings of the trachea; and a stopper configured to removably secure a proximal end of the endotracheal placement device to the proximal end of the intubation tube with the placement device extending through the intubation tube and the distal end of the endotracheal placement device extending out of the distal end of the intubation tube.

28. The intubation device of claim 27 wherein:
the stopper comprises a rubber stopper having a hole;
the stopper is configured to frictionally receive the endotracheal placement device in the hole; and
the proximal end of the intubation tube is configured to partially receive the stopper.

29. The intubation device of claim 27 wherein the stopper comprises a detachable portion of the proximal end of the intubation tube.

30. The intubation device of claim 29 wherein the intubation tube comprises a perforated border configured to facilitate detaching the detachable portion from the proximal end of the intubation tube.

31. The intubation device of claim 27 wherein the proximal end of the endotracheal placement device extends out of the proximal end of the intubation tube.

32. The intubation device of claim 27 wherein the endotracheal placement device comprises a semi-rigid rod.

33. The intubation device of claim 27 wherein a tip of the distal end of the intubation tube has a rounded shape.

34. The intubation device of claim 33 wherein the tip of the distal end of the intubation tube has an opening having a diameter approximately equal to a diameter of the endotracheal placement device.

35. The intubation device of claim 34 wherein a portion of a wall of the intubation tube adjacent to the distal end of the intubation tube has a plurality of ventilation openings.

36. The intubation device of claim 27 wherein a tip of the distal end of the intubation tube is tapered.

37. The intubation device of claim 36 wherein the tip of the distal end of the intubation tube is configured to taper to approximately a diameter of the distal end of the endotracheal placement device.

38. The intubation device of claim 37 wherein a portion of a wall of the intubation tube adjacent to the distal end of the intubation tube has a plurality of ventilation openings.

39. The intubation tube of claim 27 wherein a portion of a wall of the intubation tube adjacent to the distal end of the intubation tube has a plurality of ventilation openings.

40. The intubation tube of claim 27 wherein the intubation tube comprises an inflatable cuff and the plurality of ventilation openings are located on the wall between the distal end of the intubation tube and the inflatable cuff.

41. An intubation device, comprising:
means for introducing the intubation device through vocal cords, the means including a tactile accentuator flap; and
a stopper configured to secure a proximal end of an intubation tube to a proximal end of the means for introducing with the means for introducing extending through the intubation tube and a distal end of the means for introducing extending out of a distal end of the intubation tube.

42. The intubation device of claim 41 wherein the means for introducing comprises an intubation placement device.

43. The intubation device of claim 41 wherein the stopper comprises a rubber stopper configured to frictionally secure the means for introducing.

* * * * *